United States Patent [19]
Gupta

[11] Patent Number: 5,783,673
[45] Date of Patent: *Jul. 21, 1998

[54] METHOD OF PREFERENTIAL LABELLING OF A PHYCOBILIPROTEIN WITH AN AMINEREACTIVE DYE FOR USE IN A MULTIPLE COLOR ASSAY AND PRODUCT FOR SUCH USE

[75] Inventor: Ravinder K. Gupta, Pembroke Pines, Fla.

[73] Assignee: Coulter Corporation, Miami, Fla.

[*] Notice: The term of this patent shall not extend beyond the expiration date of Pat. Nos. 5,171,846 and 5,272,257.

[21] Appl. No.: 728,414

[22] Filed: Oct. 10, 1996

Related U.S. Application Data

[63] Continuation of Ser. No. 227,573, Apr. 14, 1994, abandoned, which is a continuation of Ser. No. 990,861, Dec. 11, 1992, abandoned, which is a continuation-in-part of Ser. No. 940,026, Sep. 3, 1992, Pat. No. 5,272,257, which is a continuation-in-part of Ser. No. 526,387, May 21, 1990, Pat. No. 5,171,846.

[51] Int. Cl.$^6$ .............. A61K 35/78; A61K 35/80; C07K 17/00; G01N 33/531
[52] U.S. Cl. .............. 530/400; 530/370; 530/395; 530/345; 530/807; 530/403; 530/404; 530/405; 530/408; 436/501; 436/536; 436/546; 435/961; 435/964
[58] Field of Search ................. 436/501, 536, 436/543, 544, 545, 546; 530/370, 345, 395, 400, 401, 403, 404, 405, 408; 435/961, 964

[56] References Cited

U.S. PATENT DOCUMENTS

| | | | |
|---|---|---|---|
| 4,520,110 | 5/1985 | Stryer et al. | 436/501 |
| 4,542,104 | 9/1985 | Stryer et al. | 436/536 |
| 4,666,862 | 5/1987 | Chan | 436/501 |
| 4,859,582 | 8/1989 | Stryer et al. | 435/5 |
| 4,981,977 | 1/1991 | Southwick et al. | 548/455 |
| 5,171,866 | 12/1992 | Gupta | 530/400 |
| 5,268,486 | 12/1993 | Waggoner et al. | 548/427 |
| 5,272,257 | 12/1993 | Gupta | 530/370 |

FOREIGN PATENT DOCUMENTS 3912046  3/1990  Germany.

OTHER PUBLICATIONS

Waggoner, Alan S. et al. (1993) PE–CY5 A New Fluorescent Antibody Label for Three–Color Flow Cytometry with a Single Laser. *Clinical Flow Cytometry* (Ann. New York Acad. Sci., Alan L. Landay, ed.) pp. 185–193.

Jean–Pierre Aubry et al., J. Immunological Method 128: 39–49 (1990), 7–Amino–4–. . . function of RNA and DNA content.

Alexander N. Glazer et al., Biophys. J. Biophysical Soc. 43: 383–386 (1983), "Fluorescent Tandem Phycobiliprotein Conjugates".

*Protein Purification* R.K. Scopes, ed. (Springer–Verlag, New York 1987), pp. 50, 166–167 176–181 and 315.

(List continued on next page.)

*Primary Examiner*—Ponnathapura Achutamurthy
*Assistant Examiner*—P. Ponnaluri
*Attorney, Agent, or Firm*—Michelle A. Kaye

[57] ABSTRACT

A method for preparing phycobiliprotein/amine-reactive dye conjugates is disclosed in which the conjugates so prepared overcome the energy transfer/fluorescent quenching dilemma encountered in the use of prior art conjugates. A phycobiliprotein, for example, phycoerythrin or allophycocyanin, is conjugated with an amine-reactive dye, for example, Texas Red or carboxyfluorescein succinimidyl ester, in the presence of a selective salt which causes a hydrophobic intramolecular rearrangement of the phycobiliprotein thereby exposing more hydrophobic sites for binding to the amine-reactive dye. The conjugates prepared according to the invention are useful in multiple color fluorescence assays without requiring the use of multiple exciting sources.

7 Claims, 5 Drawing Sheets

OTHER PUBLICATIONS

R.J. Yon, INt. J. Biochem. 9: 373–379 (1978), "Recent Developments In Protein Chromatography Involving Hydrophobic Interactions."

Becton–Dickinson Technical Brochure, Catalog No. 9026, Streptavidin DuoChrome (1990).

A.N. Glazer et al., Trends in Biochem. Sci. 9: 423–427 (1984) Phycofluor probe.

R.R. Hardy, "Purification and Coupling of Fluorescent Proteins . . . " in Handbook of Experimental and Immunol., 4th Ed., D.M. Weir, ed., vol. 1.

MacColl and Guard–Frier, *Phycobiliproteins* (CRC Press, Boca Raton, FL 1987), pp. 1–7.

I. Rosengren et al., Biochim Biophys Acta 412: 51–61 (1975), "Hydrophobic Choromatograph on Non–Charged Sepharose Derivatives."

F. Haurowitz, *The Chemistry and Function of Proteins* (Academic Press, New York 1963) pp. 154–159.

A.L. Lehninger, *Biochemistry, 2nd Ed.* (Worth, New York 1981) pp. 43–44, 62–63 and 142–145.

K.M. Gooding, BioChromatography 1: 34–40 (1986).

Southwick et al (1990) Cytometry 11:418–430.

Smith et al (1985) Nucleic Acids Res 13(7):2399–2412.

In *"Excited States of Biopolymers"* ed RF Steiner Chapter 2 pp. 29–58, Plenum Press, NY 1982, au: Haughland Covalent Fluorescent Probes.

Streptavidin DuoChrome product bulletin.

BDS Biological Detection System, Inc "FluoroLink" products Cy5 and Cy3 product description.

"TOYOPEARL" product description.

Mujumdar et al (Mar./Apr. 1993) 4(2):105–111 *Bioconjugate Chemistry* "Cyanine Dye Labeling Reagents: Sulfoindocyanine Succinimidyl Esters."

Oi et al (1982) J. Cell Biol. 93:981–986.

METHOD OF PREFERENTIAL LABELLING OF A PHYCOBILIPROTEIN WITH AN AMINEREACTIVE DYE FOR USE IN A MULTIPLE COLOR ASSAY AND PRODUCT FOR SUCH USE

RELATED APPLICATION

This is a continuation of application Ser. No. 08/227,573, filed on Apr. 14, 1994 entitled "Method of Preferential Labelling of a Phycobiliprotein with an Amine-Reactive Dye for Use in a Multiple Color Assay and Product for such Use", now abandoned, which is a continuation of Ser. No. 07/990,861, filed on Dec. 11, 1992 entitled "Method of Preferential Labelling of a Phycobiliprotein with an Amine-Reactive Dye for Use in a Multiple Color Assay and Product for such Use", now abandoned, which is a Continuation-In-Part of application Ser. No. 07/940,026, filed Sep. 3, 1992 entitled METHOD OF PREFERENTIAL LABELLING OF A PHYCOBILIPROTEIN WITH AN AMINE-REACTIVE DYE FOR USE IN A MULTIPLE COLOR ASSAY AND PRODUCT FOR SUCH USE (now U.S. Pat. No. 5,272,257, issued Dec. 21, 1993); which is a Continuation-In-Part of Ser. No. 07/526,387, filed May 21, 1990, entitled METHOD OF PREFERENTIAL LABELLING OF A PHYCOBILIPROTEIN WITH A SECOND DYE FOR USE IN A MULTIPLE COLOR ASSAY AND PRODUCT FOR SUCH USE, now U.S. Pat. No. 5,171,846, issued Dec. 15, 1992. These applications and patents are owned by a common assignee, Coulter Corporation, Hialeah, Fla.

FIELD OF THE INVENTION

This invention relates generally to electron donor-acceptor conjugates suitable for use in multiple color assay methods, particularly to a method of producing phycobiliprotein-dye conjugates suitable for such use.

BACKGROUND OF THE INVENTION

The technique of fluorescence was first introduced by Coons in 1941. He used a blue fluorescing anthracene compound coupled to pneumococcus antiserum to detect bacterial antigens in tissue section. Subsequent to this initial discovery, many fluorescing materials have been investigated, but only two, the fluorochromes fluorescein and rhodamine, are widely used, particularly in the form of fluorescein isothiocyanate (FITC) and tetramethylrhodamine isothiocyanate (TRITC) respectively. FITC covalently binds to proteins at alkaline pH through the epsilon ($\epsilon$) amino residues of lysine and through terminal amino groups. FITC's adsorption maximum is at 490–495 nm and it emits its characteristic green color at 517 nm. TRITC likewise binds to proteins, has its absorption maximum at 541 nm and emits its characteristic red color at 572 nm.

Fluorescence is the emission of light of one wavelength (color) by a substance that is being irradiated by light of a different wavelength. The emitted light is always of lower energy, hence longer wavelength, then the incident light. In clinical use, the strength of the fluorescence is dependent on the efficiency with which the fluorochrome transforms incident light into emitted light, the amount of dye present in the specimen under observation and the intensity of the incident light. The dye known as Texas Red (sulforhodamine 101 sulfonyl chloride or sulforhodamine acid chloride) has previously been investigated for clinical use in conjugation with phycoerythrins, but major problems were encountered. These problems were low fluorescent efficiency, inadequate energy transfer from the phycoerythrin to Texas Red and the instability of the phycoerythrin-Texas Red conjugate. Phycoerythrin-Texas Red conjugates are desirable, however, because the overlap of their absorption and emission spectra have the potential to give a strong fluorescence signal.

Low fluorescent efficiency occurs whenever fluorescent chromophores are spatially adjacent to each other. It is usually called concentration quenching. See R. P. Hughland, "Excited States of Biopolymers", R. F. Steins, Ed., p 47 (Plenum Press, New York, 1983). However, high levels of labelling, resulting in chromophores being spatially adjacent to each other, are required in order to assure adequate energy (electron) transfer from the phycoerythrin to the acceptor dye chromophore. The net result is that the trade off required by the opposing effects results in less than optimal performance. Recently, A. N. Glazer et al. have covalently linked a phycoerythrin to an allophycocyanin to produce a highly fluorescent tandem conjugate with an energy transfer efficiency of 90%. See A. N. Glazer et al., T.I.B.S, 9:423 (1984); Biophysics J., 43,386–386 (1983); and U.S. Pat. No. 4,542, 104 (See also U.S. Pat. No. 4,520,110 to L. Stryer et al. describing the use of phycobiliproteins as fluorescent probes for the analysis and separation of molecules and cells). However, forming a conjugate from two naturally occurring pigments derived from algae is much different from conjugating a synthetic dye such as Texas Red. In fact, the procedures usually followed for conjugating reactive dyes to proteins does not work with phycoerythrin-Texas Red. Using such procedures, one obtains a complex with a low energy transfer efficiency at low levels of labelling or fluorescence quenching at high levels of labelling. Texas Red forms a conjugate with a phycoerythrin by reaction of its sulfonyl or acid chloride moiety with an amine group of phycoerythrin or other phycobiliprotein.

Phycobiliprotein/amine-reactive dye conjugates are known and some, for example, phycoerythrin-Texas Red conjugates, are commercially available. For example, the phycoerythrin-Texas Red conjugate known as Duo-CHROME™ is available bound to streptavidin from Becton Dickinson Immunology Systems, Mountain View, Calif. (Catalog No. 9026). The available conjugates, however, suffer from the fact that they do not have a uniform phycoerythrin-Texas Red ratio throughout the individual conjugate members. There are present overlabelled and underlabelled species as well as species having the desired or optimum degree or range of labelling. Consequently, energy transfer/quenching problems can arise depending upon the distribution of labelled species within the entire sample.

This invention solves the energy transfer/quenching problem encountered in the preparation of phycobiliprotein/amine-reactive conjugates in general by preferentially labelling sites close to the chromophore regions of a phycobiliprotein with an amine-reactive dye and separating overlabelled and underlabelled conjugates from conjugates having the desired degree of labelling by chromatographic methods; for example, by exploiting the differences in hydrophobic character of conjugates having different degrees of labelling.

SUMMARY OF THE INVENTION

A method is provided for preparing a phycobiliprotein/amine-reactive dye (PARD) conjugate which overcomes the problems relating to the energy transfer/fluorescent quenching phenomenon encountered in such conjugates. An amine-reactive dye, such as Texas Red or a carboxyfluoroscein succinimidyl ester, is reacted with a phycobiliprotein, such as a phycoerythrin or an allophycocyanin, in the presence of a salt especially selected to cause an intramolecular rearrangement of the phycobiliprotein structure whereby to expose a multiplicity of sites in its hydrophobic region with which said dye can bind to form the desired conjugate. The reaction is controlled as to the anion of the selected salt, permitted time of reaction and temperature. Conjugates having the preferred degree of phycobiliprotein/amine-reactive dye conjugation are separated from overlabelled and under-labelled conjugates by hydrophobic interaction chromatography. Alternatively, hydrophobic interaction chromatography may be used to separate conjugates having the desired degree of labelling from a reaction mixture which did not use the selective salts taught herein.

DETAILED DESCRIPTION OF THE INVENTION

Figure 1:
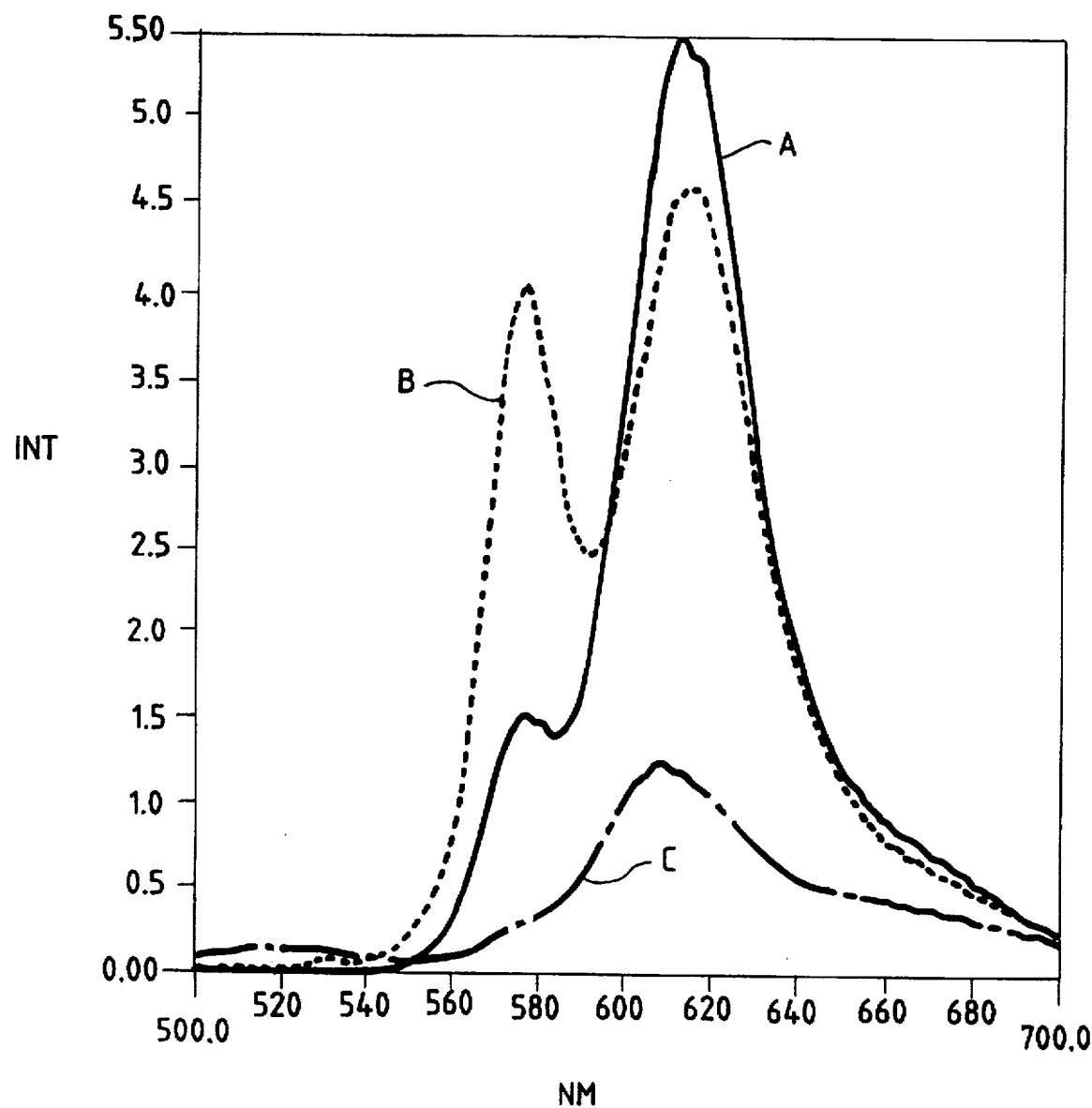
FIG. 1 illustrates the spectral differences between the PETR conjugate of the invention (A) and commercially available conjugates (B,C).

The first feature of this invention, preferential site labelling, makes it possible to obtain a satisfactory level of energy transfer from a phycobiliprotein to an amine-reactive dye even at low levels of dye conjugation by bringing the dye and the chromophore of the phycobiliprotein into close proximity. This is accomplished by making use of the hydrophobic tetrapyrrole (bilin) chromophores that biliproteins are known to possess. See R. McColl and D. Guard-Frier, Phycobiliproteins, Chapter 1, C.R.C. Press (1987). Specifically, when certain anions commonly used in some "salting-out" processes are added to a phycobiliprotein containing buffer solution, they cause the phycobiliprotein to undergo an intramolecular structural rearrangement which "opens-up" or "exposes" hydrophobic sites on the protein by reducing steric hindrance about the site. As a result of this hydrophobic intramolecular rearrangement, the sites close to chromophores can more readily react with a reactive dye, such as Texas Red, to form a conjugate. The common ions used in this process may be any of the common ions used in "salting-out" processes, such as phosphate, acetate, citrate, sulfate, tartrate and the like. The preferred anions are sulfate, phosphate and acetate. The most preferred anion is sulfate because it has little or no effect on the pH of the solution. The exact amount of anion required in a given reaction is dependent on the particular phycobiliprotein undergoing reaction. For example, when using the sulfate in a phycoerythrin-Texas Red (PETR) conjugation reaction, it was found that an anion concentration in the range of about 1% to about 4% in the reaction solution resulted in a PETR conjugate having significantly improved energy transfer efficiency as compared to a PETR control conjugate prepared in the absence of a preferred anion. On the other hand, allophycocyanin requires the use of about 8% to 12% sodium sulfate. Using the principles taught herein, the optimal concentration of the selected salt can easily be determined. Overall, the optimal concentrations will range between 1% and about 20%.

The phycobiliprotein and the amine-reactive dye are reacted together at a pH greater than 7 for a time in the range of 10 minutes and at a temperature of about 4° C. to about 25° C. prior to sampling to determine if an overall adequate phycobiliprotein-dye conjugation ratio has been reached. The preferred pH is greater than 8 and less than 12. The determination is carried out by chromatographically removing excess dye from a sample of the reaction mixture and spectroscopically determining an absorbance ratio, $A_x/A_y$, defined as the ratio of the intensity of the maximum absorption of the phycobiliprotein divided by the intensity of the maximum adsorption of the amine-reactive dye. For a PETR conjugate, $A_x/A_y$ is $A_{565}/A_{595}$. If the value of $A_{565}/A_{595}$ is in the range of 2.9 to 3.2, the reaction mixture is quenched and excess dye is removed. The $A_x/A_y$ value will differ for different PARD conjugates. The removal of the excess dye simultaneously removes excess salts such as the sodium sulfate preferably used to expose a phycobiliprotein's hidden hydrophobic sites.

An excess of amine-reactive dye is used in the claimed method. The initial molar ratio of amine-reactive dye to phycobiliprotein in the reaction mixture is in the range of about 5:1 to about 30:1.

A phycobiliprotein/amine-reactive dye conjugate is formed by reaction of an amino group on the phycobiliprotein with a reactive group present on the amine-reactive dye. For example, a phycoerythrin-Texas Red conjugate is formed by reaction of an amino group on phycoerythrin with the sulfonyl or acid moiety of Texas Red. The reactivity of phycobiliprotein amino groups is well known. For example, small biomolecules such as biotin have been attached to phycobiliproteins by reaction with an appropriate activated ester or sulfonyl chloride derivative. The reaction between phycobiliproteins and amine-reactive dyes as taught herein, for example, the reaction between phycoerythrin and Texas Red, is analogous to the biotin reaction and to the reactions of fluorescein isothiocyanate with the ε-amino residues of lysine and terminal amino groups previously mentioned. While any moiety reactive with amines may be used according to the invention, the preferred reactive moieties present on the amine-reactive dye are selected from the group consisting of sulfonic and carboxylic acids and their acid chlorides and esters. Specific examples of such dyes include 5- or 6-carboxyl-x-rhodamaine succinimidyl esters, sulforhodamine 101 sulfonyl chloride, Lissemine rhodamine B sulfonyl chloride. Compounds such as fluorescein-5-isothiocyanate and fluorescein-6-isothiocyanate, are further examples of amine-reactive dyes.

Phycobiliproteins is general may be used according to the invention. In addition to phycoerythrin and allophycocyanin used in the Examples herein, C-phycocyanin, R-phycocyanin and phycoerythrocyanin, among others, may be reacted as described herein.

The separation of over-labelled and under-labelled PARD conjugate species from those having the desired degree of labelling was accomplished using hydrophobic interaction chromatography with an appropriate column medium like butyl TOYOPEARL™ (Toso Haas, Philadelphia, Pa.). The PARD conjugate produced by this method can be used in conjunction with an antibody to stain different types of cell. The cells so stained will be dependent upon the choice of antibody. The importance of the invention lies in the fact that PARD conjugates provide for an additional color in fluorescence analysis with the use of only a single excitation wavelength, which wavelength is determined by the choice of the amine-reactive dye. For example, FITC, R-phycoerythrin PETR and APC-FSE can be excited with a single excitation wavelength (laser) of 488 nm to emit maximally at about 525, 575, 612 and 660 nm respectively. As a result of this feature, the expense of multiple excitation sources is eliminated.

PREFERRED EMBODIMENTS OF THE INVENTION

Example 1

Reaction of Phycoerythrin and Texas Red

In a typical reaction, a purified R-phycoerythrin (PE) solution [3.0 g PE, 45.04 ml solution; PE concentration is 66.6 mg/ml in 2 mM EDTA-PBS (PBS=Phosphate Buffered Saline)] was cooled in ice-bath and treated dropwise, with stirring, with an ice-cold solution of PBS containing 2 mM EDTA (29.25 ml), 20% $Na_2SO_4$ (pH 7.0, 6.0 ml) and 1M potassium borate (pH 9.80, 30 ml). To the resulting mixture was added with vigorous stirring and at 4° C. a 25-fold molar excess of Texas Red (20 mg/ml in anhydrous dimethylformamide). The reaction was monitored by drawing 10 µL samples periodically and removing excess dye on a 0.5–2 ml Sephedex® G-50 column in PBS. The protein containing peak was collected and its $A_{565}/A_{595}$ value determined spectrophotomet If the $A_{565}/A_{595}$ values remain above 3.2, even after 30 minutes or more of reaction time, a further aliquot of Texas Red solution of 1–5 times the initial PE concentration was added to the reaction mixture.

When $A_{565}/A_{595}$ value fell below 3.2, preferably in the range of 2.9–3.2, the reaction may be quenched by addition of an one-hundred fold molar excess of a quenching agent glycine to the reaction mixture. Typical quenching agents are glycine, hydroxylamine hydrochloride, ethanolamine and lysine among others. Excess reactive dye was next removed by passing the reaction mixture through a SEPHADEX® G-50 column in PBS, 2 mM EDTA. The phycoerythrin-Texas Red conjugate, in the protein peak, was then chromatographically factionated on a butyl 650M chromatographic column by eluting with a reverse gradient (3% to 0%) of sodium sulfate in 100 mM potassium phosphate solution containing 2 mM EDTA at pH 7.0±0.1. Butyl 650M is an abbreviation of butyl TOYOPEARL™ 650M available from Toso Haas). Chromatographic fractions having the desired emission characteristics (high energy transfer and high quantum efficiency) were pooled, concentrated, dialyzed against PBS, 2 mM EDTA and reconcentrated to give a purified phycoerythrin-Texas Red conjugate. The purified PETR conjugate was used as a marker in fluorescent immunoassays. The PETR marker can be conjugated to protein-like substances such as antibodies and streptavidin using methods known in the art. FIG. 1 illustrates the emission spectra differences between the PETR conjugate made according to the invention and commercially available conjugates (B, Southern Biotechnology Associates; C, Becton-Dickinson).

Example 2

Reaction of Allophycocyanin (APC) with a Carboxyfluorescein Succinimidyl Ester (FSE)

6.25 ml (292.4 mg) APC solution (46.748 mg/ml in PBS, 2 mM EDTA) was treated by dropwise addition, with stirring, of a solution resulting from mixing PBS, 2 mM EDTA (6.17 ml), 1M potassium borate of pH 9.80 (7.3 ml) and 20 wt % sodium sulfate of pH 7.0 (8.76 ml). A 14-fold excess of FSE (25 mg/ml in anhydrous dimethylforamide) was added to the APC solution at room temperature (about 22° C.). After 30 minutes, a 50 µL sample of the reaction mixture was withdrawn, excess dye removed on a SEPHADEX® G-50 column in PBS which was 2 mM in EDTA, and the protein $A_{496}/A_{652}$ value for the protein peak was checked.

If the $A_{496}/A_{652}$ ratio is less than 0.5 after 60 minutes or more reaction time, an additional aliquot of FSE was added to the reaction mixture. When an $A_{496}/A_{652}$ value in the range of 0.5–0.7 is achieved, the reaction is stopped by removing excess dye on a SEPHADEX® G-50 column in PBS, 2 mM EDTA. Alternatively, a quenching agent is added to the reaction mixture prior to passage through the Sephadex® column. The protein peak is collected and the APC-FSE conjugate mixture is further fractionated using hydrophobic interaction chromatography on a butyl 650S (Toso Haas) column using a reverse gradient (4% to 0%) sodium sulfate in 100 mM potassium phosphate, 2 mM EDTA of pH 7.0±0.1, followed by steps of 50 mM potassium phosphate, 2 mM EDTA of pH 7.0±0.1, and lastly, PBS, 2 mM EDTA. Fractions showing high energy transfer efficiency and high fluorescence were found to have an $A_{496}/A_{652}$ ratio of about 0.4–0.6. These were pooled, dialyzed against PBS, 2 mM EDTA and concentrated. The yield was 54%. The conjugate was used without further purification.

Example 3

APC-FSE Conjugate Prepared Without Using Selected Salts

APC and FSE are reacted as in Example 2, but without the addition of the selected salt. The reaction time is extended within the range of 0.5 to 5.0 hours after the addition of FSE to APC is completed. The reaction mixture is then passed through a SEPHADEX® G-50 column and is subsequently fractionated by hydrophobic interaction chromatography. Fractions having $A_{496}/A_{652}$ in the range of 0.4–0.6 are collected, dialyzed and concentrated, and may be used without further purification. The yield is lower than in Example 2 where selected salts were used and is estimated to be about 35% at a maximum.

Example 4

Reaction of R-Phycoerythrin with the Amine-Reactive Dye Cy5.18-OSu 1 ml (50 mg) of purified R-phycoerythrin solution (PE, 50 mg/ml 2 mM EDTA), cooled to 0° C. in an ice bath, was treated by dropwise addition, with stirring, with a 0° solution resulting from mixing a 1M borate-PBS solution (pH 9.8, 3.125 ml), 2 mM EDTA (4.45 ml) and 20% $Na_2SO_4$ (pH 7.0, 0.625 ml). A 10-fold molar excess of Cy5.18-OSu (hereafter CY, 1 mg/ml in PBS, 2 mM EDTA, available as Cy5™ Cy5.18-OSu (5,5'-Bis-sulfo-1,1'-bis(ε-carboxypentynyl)-3, 3,3',3'-tetramethylindodicarbocyanine disuccinimidyl ester) from Biological Detection Systems, Inc., Rockville, Md.;) was added to the resulting R-phycoerythrin solution. Reaction progress was monitored by periodically taking a 50 µL sample of the reaction mixture, desalting the sample on a Sephadex® G-50 column in PBS which is 2 mM in EDTA, collect- ing the protein peak and spectroscopically determining the protein $A_{565}/A_{665}$. If the value is more than 2.3 after 10 minutes of reaction, another 1- to 5-fold excess of CY, relative to the initial PE quantity, was added to the reaction mixture. About 1–4% of a selected salt is used in the preparation of PE/CY.

When $A_{565}/A_{651}$ value is in the range of 1.6–2.3, the reaction mixture was desalted on a SEPHADEX® G-50 column in PBS which is 2 mM in EDTA. Alternatively a quenching agent such as hydroylamine or 2-aminoethanol is added to the reaction mixture before desalting on SEPHADEX® G-50 as described. The protein peak is collected and the PE-CY conjugate is further fractionated using hydrophobic interaction chromatography on a Butyl 650S column using a reverse gradient (4.5% to 0% w/v) sodium sulfate solution which is 100 mM in potassium phosphate, 2 mM EDTA and pH 7.0±0.1. The chromotographic fractions were checked for emissions at 575 nm (PE) and 665 nm (CY) using a 488 nm excitation source. The fractions having high energy transfer efficiency ($E_{575}/Em_{665} \leq 0.15$) and high energy transfer efficiency were combined, concentrated, dialyzed against PBS, 2 mM EDTA and reconcentrated.

Figure 2:
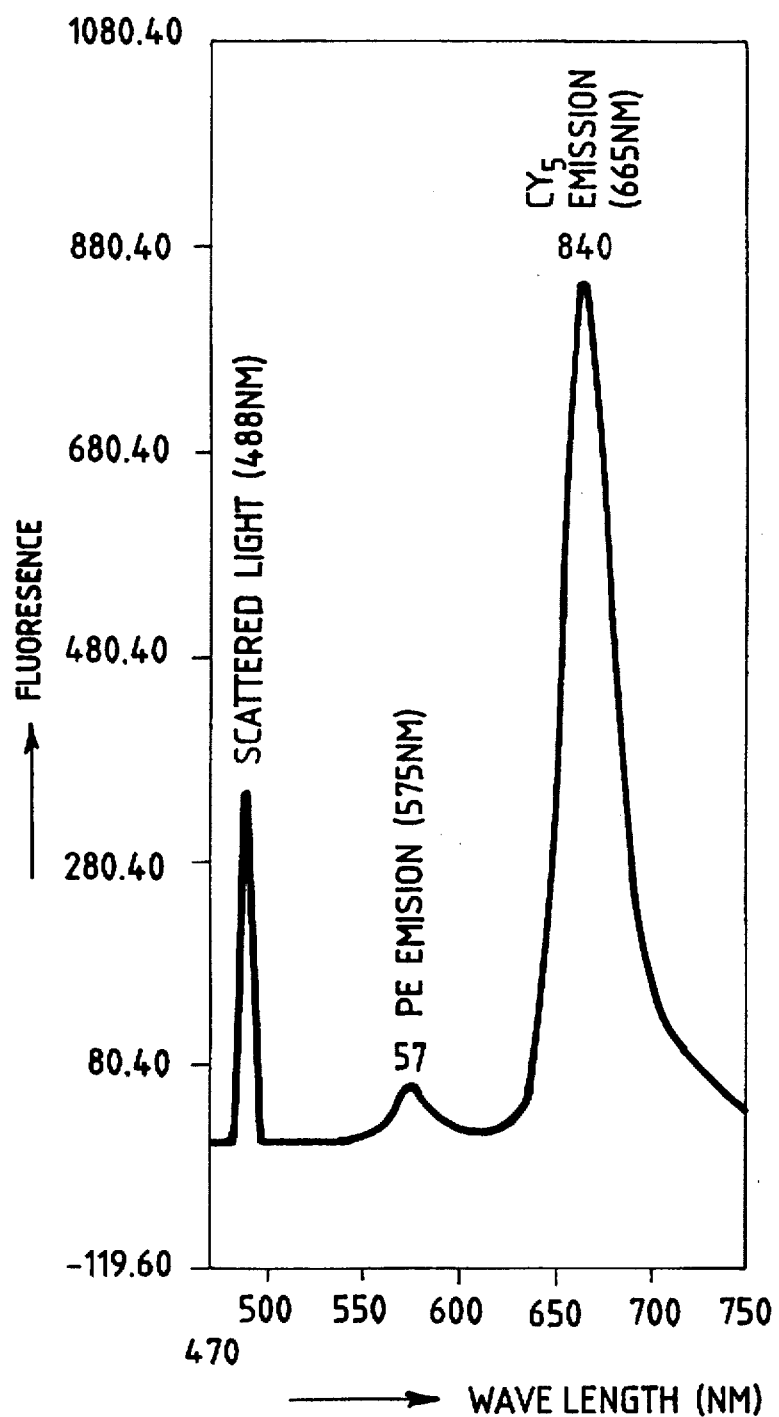
FIG. 2 illustrates the emission spectrum of the R-phycoerythrin/Cy5.18-OSu conjugate after excitation at λ=488 nm.

The spectrum of the product from a typical preparation, FIG. 2, shows about 93–96% energy transfer efficiency ($Em_{575}/Em_{665}$=about 0.04 to about 0.07). The PE/CY product can then be conjugated to proteins such as antibodies by method known to those skilled in the art and used in various analytical methods such as flow cytometry.

TABLE 1

Figure 3:
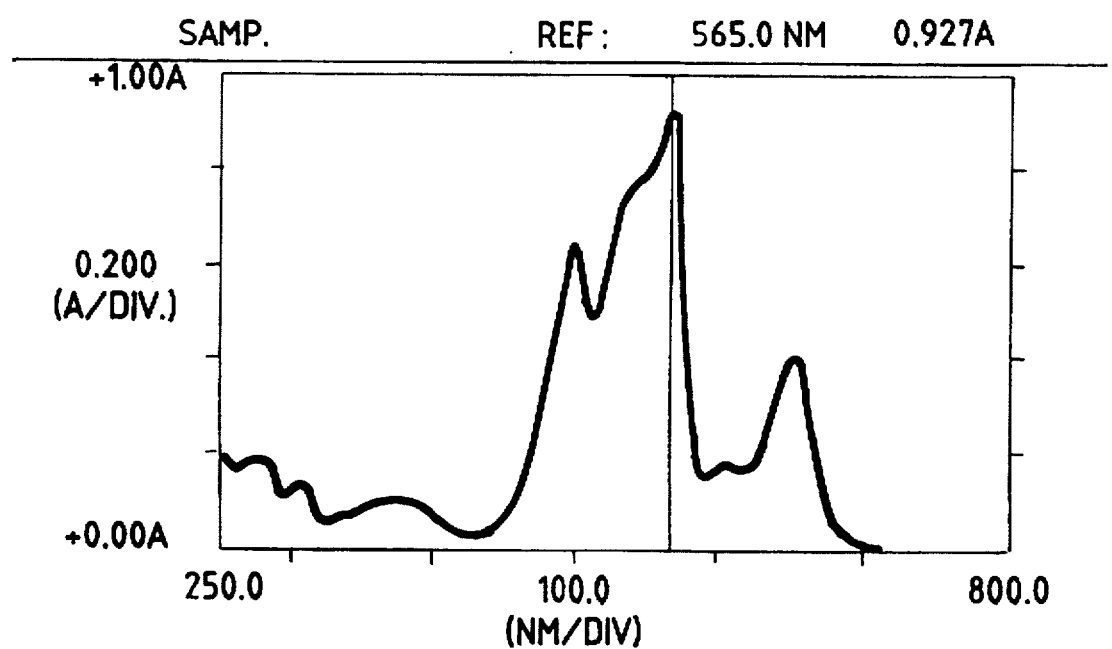
FIG. 3 illustrates the adsorption spectrum of the R-phycoerythrin/Cy5.18-OSu conjugate.
Figure 4:
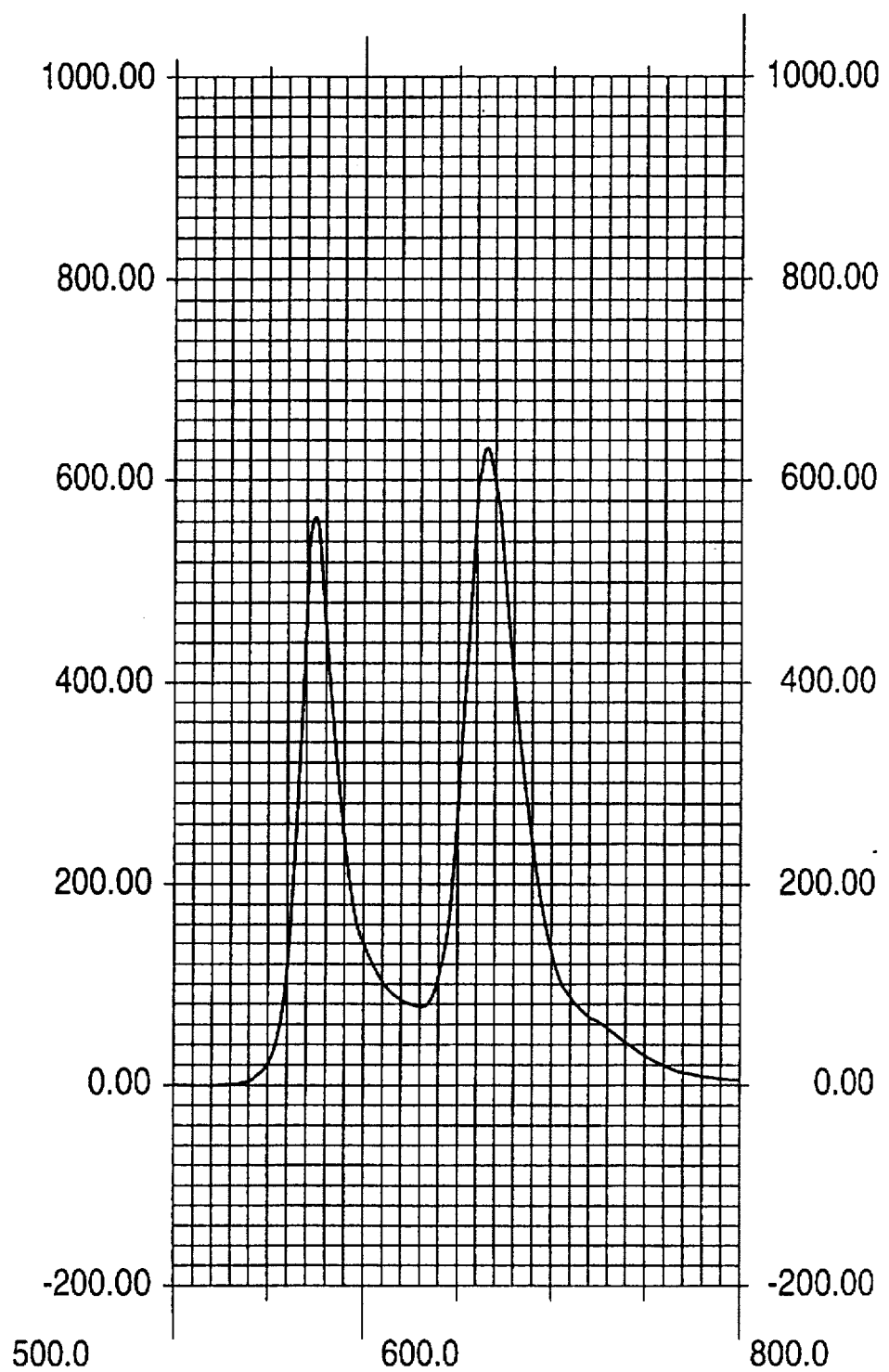
FIG. 4 illustrates the fluorescence spectrum for underconjugated fraction of the PE-Cy5.18 conjugate, separated by hydrophobic interaction chromatography.
Figure 5:
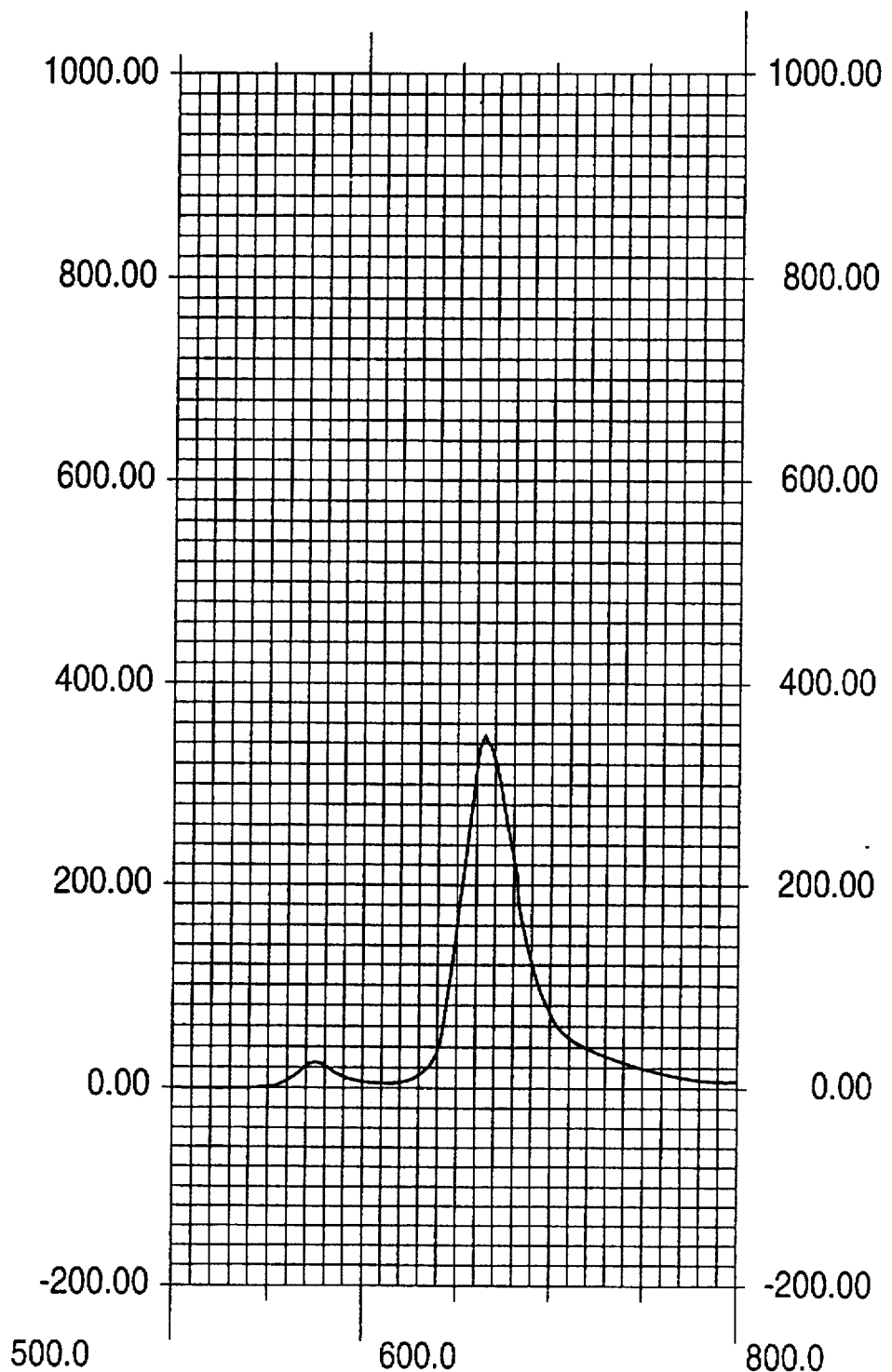
FIG. 5 illustrates the fluorescence spectrum for overconjugated fraction of the PE-Cy5.18 conjugate, separated by hydrophobic interaction chromatography.

Peaks & Valleys in Absorption Spectrum of PE/CY (FIG. 3).

| PEAK | | VALLEY | |
|---|---|---|---|
| λ | ABS | λ | ABS |
| 651.0 | 0.398 | 779.0 | −0.002 |
| 607.0 | 0.175 | 618.0 | 0.166 |
| 568.0 | 0.928 | 592.0 | 0.151 |
| 497.0 | 0.647 | 510.0 | 0.483 |
| 369.0 | 0.104 | 425.0 | 0.025 |
| 278.0 | 0.184 | 324.0 | 0.059 |
| | | 263.0 | 0.160 |

I claim:

1. A method of producing a phycobiliprotein-amine reactive dye conjugate which method comprises reacting the phycobiliprotein with the amine reactive dye, desalting the reaction mixture to remove the dye not conjugated with the phycobiliprotein, and further separating the conjugate by hydrophobic interaction chromatography in order to separate out phycobiliprotein underlabelled and overlabelled with amine reactive dye from that having the desired degree of labelling with the amine reactive dye.

2. The method according to claim 1 wherein the phycobiliprotein is phycoerythrin and the amine reactive dye is Texas Red.

3. The method according to claim 1 wherein the phycobiliprotein is allophycocyanin and the amine reactive dye is carboxyfluorescein succinimidyl ester.

4. The method according to claim 1 wherein the phycobiliprotein is phycoerythrin and the amine reactive dye is 5,5'-Bis-sulfo-1,1'-bis(ε-carboxypentynyl)-3,3,3',3'-tetramethylindodicarbocyanine disuccinimidyl ester.

5. A method of producing a phycoerythrin-amine reactive dye conjugate which method comprises reacting the phycoerythrin with the amine reactive dye in the presence of 1 to 20% salt, desalting the reaction mixture in order to remove the dye not conjugated with the phycoerythrin and further separating the conjugate by hydrophobic interaction chromatography in order to separate out phycoerythrin underlabelled and overlabelled with amine reactive dye from that having the desired degree of labelling with the amine reactive dye.

6. The method of claim 5 wherein the amine reactive dye is 5,5'-Bis-sulfo-1,1'-bis(ε-carboxypentynyl)-3,3,3',3'-tetramethylindodicarbocyanine disuccinimidyl ester.

7. The method of claim 5 wherein said salt is one whose anion is selected from the group consisting of phosphate, sulfate, acetate, citrate and tartrate ions.

* * * * *